United States Patent
Liu et al.

(10) Patent No.: US 7,569,234 B2
(45) Date of Patent: Aug. 4, 2009

(54) HERB COMPOSITION FOR TREATING LUNG CANCER AND PREPARATION METHOD THEREOF

(75) Inventors: Jiaxiang Liu, Shanghai (CN); Jianshi Zhou, Jiangxi (CN)

(73) Assignee: Ming Qi Oncology Chinese Medicines, Inc., Brookfield, CT (US)

( * ) Notice: Subject to any disclaimer, the term of this patent is extended or adjusted under 35 U.S.C. 154(b) by 286 days.

(21) Appl. No.: 10/498,038

(22) PCT Filed: Dec. 19, 2003

(86) PCT No.: PCT/CN03/01098

§ 371 (c)(1), (2), (4) Date: Nov. 5, 2004

(87) PCT Pub. No.: WO2005/058337

PCT Pub. Date: Jun. 30, 2005

(65) Prior Publication Data

US 2005/0136132 A1    Jun. 23, 2005

(51) Int. Cl.
*A61K 36/00* (2006.01)

(52) U.S. Cl. .................................................. 424/725
(58) Field of Classification Search .............. None
See application file for complete search history.

(56) References Cited

U.S. PATENT DOCUMENTS

| 4,613,591 A | 9/1986 | Aburada et al. |
| 4,618,495 A | 10/1986 | Okuda et al. |
| 5,595,756 A * | 1/1997 | Bally et al. .................. 424/450 |
| 6,291,533 B1 | 9/2001 | Fleischner |
| 6,379,714 B1 | 4/2002 | Khwaja et al. |
| 6,495,175 B2 | 12/2002 | Rao et al. |
| 6,503,529 B1 | 1/2003 | Fleischner |

FOREIGN PATENT DOCUMENTS

| CN | 1154207 A | * | 7/1997 |
| CN | 1163129 A | * | 10/1997 |
| CN | 1179974 A | * | 4/1998 |
| DE | 10037449 A1 | * | 8/2000 |
| JP | 359036621 A | * | 2/1984 |

OTHER PUBLICATIONS

Gura, T. Systems for Identifying New Drugs are Often Faulty; Science, vol. 278, Nov. 1997, pp. 1041-1042.*

* cited by examiner

*Primary Examiner*—Patricia Leith
(74) *Attorney, Agent, or Firm*—Merchant & Gould P.C.

(57) ABSTRACT

The present invention provides a composition for treating cancers, which comprises (a) pharmaceutically acceptable carriers and (b) an effective amount of an aqueous or aqueous organic solvent extract of a crude preparation comprising *Semen Trigonellae, Astragali Radix, Glehniae Radix*, and *Asparagi Radix*. The preferred composition further comprises the extract of other anti-tumor medicinal materials, such as *Fructus Ligustri Lucidi*, or *Herba Selaginellae Doederleinii*. The present invention also provides the preparation method and use of the composition in treating cancers, especially lung cancers.

10 Claims, No Drawings

HERB COMPOSITION FOR TREATING LUNG CANCER AND PREPARATION METHOD THEREOF

FIELD OF THE INVENTION

The present invention relates to a herb preparation and composition for treating tumors/cancers and, in particular, to a medicinal herb composition for treating lung cancers containing *Semen Trigonellae* extract and the preparation method thereof.

BACKGROUND OF THE INVENTION

Currently, the available treatment methods for lung cancer include chemotherapy and radiotherapy. However, the patients suffer intense pain from such treatment while the efficacy is far from satisfactory.

U.S. Pat. No. 4,618,495 discloses a composition for reducing cancer symptoms, but not curing cancer, which comprises an aqueous or aqueous organic solvent extract of one or more crude preparations selected from the group consisting of *Astragali radix, Cinnamomi cortex, Rehmanniae radix, Paeoniae radix, Cnidii rhizoma, Atractylodis lanceae rhizoma, Angelicae radix, Ginseng radix*, and *Glycyrrhizae radix*.

U.S. Pat. No. 4,613,591 discloses a composition for increasing the anti-tumor activities of drugs such as mitomycin C and decreasing the side effects associated with their use. The composition comprises an aqueous or aqueous organic solvent extract of a crude preparation of Astragali radix, Cinnamomi cortex, Rehmanniae radix, *Paeoniae radix, Cnidii rhizoma, Atractylodis lanceae rhizoma, Angelicae radix, Ginseng radix*, and *Glycyrrhizae radix*.

U.S. Pat. No. 6,379,714 discloses botanical materials as being of a pharmaceutical grade containing fenugreek. The patent discloses the process of utilizing a whole or a selected part of the plant to form an aqueous or organic extract. The biological material can also be processed to form a powder. In general, extracts of the plant material are preferred because they are easier to dissolve in liquid pharmaceutical carriers. However, powdered plant materials are well suited for many applications where the drug is administered in a solid form, e.g., tablets or capsules.

U.S. Pat. No. 6,495,175 discloses a process for obtaining useful materials from fenugreek seeds. The patent discloses the importance of dietary fiber including extracts from fenugreek seeds. A diet having adequate amount of dietary fiber is important not only in preventing the organ dysfunction but also in the treatment and management of diseases. Fiber deficiency is known to be a detrimental factor of several dysfunction and diseases, such as heart failures, coronary artery disease, diabetes, and constipation.

Fenugreek has been used in treating colic flatulence, dysentery, diarrhea, chronic cough, diabetes, and the like. The fenugreek seed is considered to be a tonic or dietary supplement. It has also been used in post-natal care to enrich lactation in nursing mothers. Fenugreek seed has also been used as a medicine for baldness and is being used as a part of hair tonics in some countries.

U.S. Pat. Nos. 6,291,533 and 6,503,529 disclose medical use of fenugreek seed for digestive problems. It acts as a laxative that lubricates the intestine of a patient. It also has a mild anti-inflammatory effect which makes it therapeutically effective for arthritis symptoms. This herb may also reduce cholesterol levels.

None of the above prior arts discloses the use of fenugreek extract as a pharmaceutical agent for treating cancers and tumors, especially the lung cancers.

From the above discussion, it is concluded that there is no effective drug for treating cancers such as lung cancers. Therefore, there is an urgent need to develop a medicinal composition effective for treating lung cancers and/or reducing the side effects associated with such treatment.

SUMMARY OF THE INVENTION

One object of the present invention is to provide a composition effective for treating lung cancers, and methods of preparation and uses thereof.

In the first aspect, the present invention provides a composition comprising (a) a pharmaceutically acceptable carrier or carriers and (b) an effective amount of an aqueous or aqueous organic solvent extract of raw herbs, which comprises *Semen Trigonellae, Astragali Radix, Glehniae Radix*, and *Asparagi Radix*.

In another preferred embodiment, the raw herbs further comprise anti-tumor medicinal materials selected from the group consisting of *Fructus Ligustri Lucidi, Herba Selaginellae Doederleinii*, and combination thereof.

In another preferred embodiment, the raw herbs further comprise anti-tumor medicinal materials selected from the group consisting of *Herba Salviae Chinensis, Rhizoma Paridis, Salviae Chinensis Herba, Herba Hedyotidis Diffusae, Radix Sophorae Tonkinensis, Radix Sophorae Flavescentis*, and combination thereof.

In another preferred embodiment, the raw herbs further comprise immunity-enhancing medicinal materials selected from the group consisting of *Radix Ophiopogonis, Herba Gynostemmae, Fructus Corni, Herba Epimedii*, ginseng, Rhizome of Largehead *Atractylodes*, and combination thereof.

In another preferred embodiment, the crude raw herbs comprise 0.5-5 parts by weight *Semen Trigonellae*, 2-20 parts by weight *Astragali Radix*, 2-10 parts by weight *Glehniae Radix*, 1-5 parts by weight *Asparagi Radix*, 0.5-5 parts by weight *Fructus Ligustri Lucidi*, and 1-10 parts by weight *Herba Selaginellae Doederleinii*.

In another preferred embodiment, the raw herbs further comprise 1-10 parts by weight *Herba Salviae Chinensis*, 1-5 parts by weight *Rhizoma Paridis*, 1-5 parts by weight *Salviae Chinensis Herba*, 1-10 parts by weight *Herba Hedyotidis Diffusae*, 1-5 parts by weight *Radix Sophorae Tonkinensis*, 1-5 parts by weight *Radix Sophorae Flavescentis*, or combination thereof; and 0.5-10 parts by weight *Radix Ophiopogonis*, 0.5-5 parts by weight *Herba Gynostemmae*, 0.5-5 parts by weight *Fructus Corni*, 0.5-5 parts by weight *Herba Epimedii*, 0.5-5 parts by weight ginseng, 0.5-5 parts by weight Rhizome of Largehead *Atractylodes*, or combination thereof.

In another preferred embodiment, the raw herbs comprise:

0.5-5 parts by weight *Semen Trigonellae*, 2-20 parts by weight *Astragali Radix*, 2-10 parts by weight *Glehniae Radix*, and 1-5 parts by weight *Asparagi Radix*;

0.5-5 parts by weight *Fructus Ligustri Lucidi*, and 1-10 parts by weight *Herba Selaginellae Doederleinii*;

1-10 parts by weight *Herba Salviae Chinensis*, and 1-5 parts by weight *Rhizoma Paridis*; and 0.5-10 parts by weight *Radix Ophiopogonis*, 0.5-5 parts by weight *Herba Gynostemmae*, 0.5-5 parts by weight *Fructus Corni*, and 0.5-5 parts by weight *Herba Epimedii*.

In another preferred embodiment, the raw herbs comprise:

0.7-3 parts by weight *Semen Trigonellae*, 2.5-10 parts by weight *Astragali Radix*, 2.5-6 parts by weight *Glehniae Radix*, and 1.2-3.5 parts by weight *Asparagi Radix*;

0.7-3 parts by weight *Fructus Ligustri Lucidi*, and 2.5-6 parts by weight *Herba Selaginellae Doederleinii*;

2-8 parts by weight *Herba Salviae Chinensis*, and 1.2-3.5 parts by weight *Rhizoma Paridis*;

0.7-5 parts by weight *Radix Ophiopogonis*, 0.7-3 parts by weight *Herba Gynostemmae*, 0.7-3 parts by weight *Fructus Corni*, and 0.7-3 parts by weight *Herba Epimedii*.

In the second aspect, the present invention provides a method for preparing a composition comprising (a) a pharmaceutically acceptable carrier or carriers and (b) an effective amount of an aqueous or aqueous organic solvent extract of raw herbs comprised of *Semen Trigonellae, Astragali Radix, Glehniae Radix*, and *Asparagi Radix*, wherein the method comprises the following steps:

(a) mixing the raw herbs with water or aqueous solution containing 30-85% (v/v) ethanol for 12-48 hours to form a mixture;

(b) filtering the mixture to obtain the filtrate and adjusting the pH of filtrate to 4-8, thereby obtaining an extract; or alternately adjusting the pH of mixture to 4-8 and filtering the mixture to obtain the filtrate, thereby obtaining an extract; and (c) mixing the extract with pharmaceutically acceptable carriers, thereby forming a composition.

In another preferred embodiment, step (b) further comprises the step of drying the obtained extract.

In another preferred embodiment, the raw herbs further comprise medicinal materials selected from the group consisting of *Fructus Ligustri Lucidi, Herba Selaginellae Doederleinii*, and combination thereof; anti-tumor medicinal materials selected from the group consisting of *Herba Salviae Chinensis, Rhizoma Paridis, Salviae Chinensis Herba, Herba Hedyotidis Diffusae, Radix Sophorae Tonkinensis, Radix Sophorae Flavescentis* and combination thereof; and immunity-enhancing medicinal materials selected from the group consisting of *Radix Ophiopogonis, Herba Gynostemmae, Fructus Corni, Herba Epimedii*, ginseng, Rhizome of Largehead *Atractylodes*, and combination thereof.

In the third aspect, the present invention provides a method for treating cancer comprising administering the composition to the patient in need. The composition comprises (a) pharmaceutically acceptable carriers and (b) an effective amount of an aqueous or aqueous organic solvent extract of raw herbs comprising *Semen Trigonellae*.

The composition preferably further comprises *Astragali Radix, Glehniae Radix*, and *Asparagi Radix*. The composition more preferably further comprises *Fructus Ligustri Lucidi* and *Herba Selaginellae Doederleinii*. The composition most preferably further comprises any anti-tumor medicinal materials such as *Herba Salviae Chinensis, Rhizoma Paridis, Salviae Chinensis Herba, Herba Hedyotidis Diffusae, Radix Sophorae Tonkinensis, Radix Sophorae Flavescentis* or combination thereof, and immunity-enhancing medicinal materials such as *Radix Ophiopogonis, Herba Gynostemmae, Fructus Corni, Herba Epimedii*, ginseng, Rhizome of Largehead *Atractylodes* or combination thereof.

In another preferred embodiment, the effective amount of the medicinal composition of the invention is 1-3 dosages per person per day, and each dosage is equivalent to 0.5-15 grams (preferably 1-10 grams) of dry *Semen Trigonellae*.

In the fourth aspect, the present invention provides the use of the medicinal composition and *Semen Trigonellae* in preparing medication for treating tumors and cancers, especially lung cancers.

DETAILED DESCRIPTION OF INVENTION

The inventors have discovered that the aqueous or aqueous organic solvent extract of *Semen Trigonellae* has a very good anti-tumor/anti-cancer activity and can effectively enhance the immunity of tumor patients. On the basis of said discovery, the inventors herein disclose the invention.

In another preferred embodiment, the invention may further comprise an aqueous or aqueous organic solvent extract of raw herbs comprising *Astragali Radix, Glehniae Radix, Asparagi Radix, Fructus Ligustri Lucidi, Herba Selaginellae Doederleinii* or combination thereof. Preferably, the extract of the invention further comprises the extract of *Astragali Radix, Glehniae Radix*, and *Asparagi Radix*. These extracts provide better efficacy against lung cancers.

In general, each raw herb exists in the mixture in the following quantity (parts by weight):

|  | parts by weight | preferred parts by weight |
| --- | --- | --- |
| *Semen Trigonellae* | 0.5-5 | 0.7-3 |
| *Astragali Radix* | 2-20 | 2.5-10 |
| *Glehniae Radix* | 2-10 | 2.5-6 |
| *Asparagi Radix* | 1-5 | 1.2-3.5 |
| *Fructus Ligustri Lucidi* | 0.5-5 | 0.7-3 |
| *Herba Selaginellae Doederleinii* | 1-10 | 2.5-6 |

In one preferred embodiment, the composition of the invention further comprises an aqueous or aqueous organic solvent extract of additional anti-tumor medicinal materials. Exemplary anti-tumor medicinal materials include, but are not limited to, *Herba Salviae Chinensis, Rhizoma Paridis, Salviae Chinensis Herba, Herba Hedyotidis Diffusae, Radix Sophorae Tonkinensis, Radix Sophorae Flavescentis* or a combination thereof.

In general, the amount of these additional anti-tumor medicinal materials is as follows:

|  | parts by weight | preferred parts by weight |
| --- | --- | --- |
| *Herba Salviae Chinensis* | 1-10 | 2-8 |
| *Rhizoma Paridis* | 1-5 | 1.2-3.5 |
| *Salviae Chinensis Herba* | 1-5 | 1.2-3.5 |
| *Herba Hedyotidis Diffusae* | 1-10 | 2-8 |
| *Radix Sophorae Tonkinensis* | 1-5 | 1.2-3.5 |
| *Radix Sophorae Flavescentis* | 1-5 | 1.2-3.5 |

In another preferred embodiment, the composition of the invention further comprises an aqueous or aqueous organic solvent extract of additional immunity-enhancing medicinal materials. Exemplary immunity-enhancing medicinal materials include, but are not limited to, *Radix Ophiopogonis, Herba Gynostemmae, Fructus Corni, Herba Epimedii*, ginseng, Rhizome of Largehead *Atractylodes*, or a combination thereof.

In general, the amount of these additional immunity-enhancing medicinal materials is as follows:

|  | parts by weight | preferred parts by weight |
| --- | --- | --- |
| Radix Ophiopogonis | 0.5-10 | 0.7-5 |
| Herba Gynostemmae | 0.5-5 | 0.7-3 |
| Fructus Corni | 0.5-5 | 0.7-3 |
| Herba Epimedii | 0.5-5 | 0.7-3 |
| ginseng | 0.5-5 | 0.7-3 |
| Rhizome of Largehead Atractylodes | 0.5-5 | 0.7-3 |

In one embodiment, the preferred extract of the invention is made from a mixture which comprises the following medicinal materials:

|  | parts by weight | preferred parts by weight |
| --- | --- | --- |
| Semen Trigonellae | 0.5-5 | 0.7-3 |
| Astragali Radix | 2-20 | 2.5-10 |
| Glehniae Radix | 2-10 | 2.5-6 |
| Asparagi Radix | 1-5 | 1.2-3.5 |
| Fructus Ligustri Lucidi | 0.5-5 | 0.7-3 |
| Herba Selaginellae Doederleinii | 1-10 | 2.5-6 |
| Herba Salviae Chinensis | 1-10 | 2-8 |
| Rhizoma Paridis | 1-5 | 1.2-3.5 |
| Radix Ophiopogonis | 0.5-10 | 0.7-5 |
| Herba Gynostemmae | 0.5-5 | 0.7-3 |
| Fructus Corni | 0.5-5 | 0.7-3 |
| Herba Epimedii | 0.5-5 | 0.7-3 |

As used in this disclosure and the claims, the term "raw herbs", which is also known as "medicinal materials" are defined as follows:

*Semen Trigonellae*: dry mature seed of *Trigonelta Foenumgraecum* (*Leguminosae* plant).

*Astragali Radix, Radix Astragali* or *Astragalus* root: Root of *Astragalus Membranaceus Bunge* or other varieties (genus *Leguminosae*, family Leguminosae).

*Glehniae Radix*: root of *GlehniaLlittoralis* (family Umbelliferae).

*Asparagi Radix*: root of *AsparagusCochinchinensis* (family Liliaceae).

*Fructus Ligustri Lucidi*: fruit of *Ligustrum Lucidum Ait* (family Oleaceae).

*Herba Selaginellae Doederleinii*: whole herb of *Selaginella Doederleinii Hieron* (family Selaginellaceae).

*Herba Salviae Chinensis*: whole herb of *Salvia Chinensis Benth* (family Labiatae).

*Rhizoma Paridis*: root or stem of *Paris Polyphylla Smith* or other varieties (family Liliaceae).

*Radix Ophiopogonis*: root of *Ophiopogon Japonicus Ker-Gawl* (family Liliaceae).

*Herba Gynostemmae*: whole herb of *Gynostemma Pentaphyllum Makino* (family Cururbitaceae).

*Fructus Corni*: fruit of *Cornus Officinalis seib. et zucc* (family Cornaceae).

*Herba Epimedii*: the overground part of *Epimedium Brevicornu Maxim* or other varieties (family Berberidaceae).

*Salviae Chinensis Herba*: pistil or whole herb of *Prunella Vulgaris Linn.*

*Herba Hedyotidis Diffusae*: root-containing whole herb of *Hedyotis Diffusa Willd.*

*Radix Sophorae Tonkinensis*: root of *Sophora Subprostrata Chun* or other varieties.

*Radix Sophorae Flavescentis*: root of *Sophora Flavescens Ait.* or other varieties.

Ginseng: root of *Panax Ginseng*.

Rhizome of Largehead *Atractylodes*: root or stem of *Atractylodes Macrocephala Koidz*.

The active ingredient of the invention, i.e., the extract of the raw herbs, can be prepared as follows: extracting the desired raw herbs with water or aqueous solution containing 30-85% (v/v) water miscible organic solvent such as alcohol (e.g., ethanol); filtering the extracted solution and drying the filtrate by selected conventional methods such as spray drying, lyophilization, or concentration-and-drying. The active ingredient of the invention can be prepared by mixing each extract of raw herbs or by extracting the mixture of raw herbs.

The extraction can be carried out at room temperature or under heated conditions, preferably at 4-35° C., more preferably at 5-30° C.

One preferred method of extraction is percolation described as follows:

Raw herbs pulverized as powder (average grain diameter 200-1000 μm, preferably 250-850 μm) are placed into a cylindrical container which has a partition at the bottom. Use ethanol aqueous solution as solvent to flow from the top downward through the powder placed on the partition. The concentration of the solvent is 30-85% (v/v), preferably 40-70%, and more preferably 45-65%. The amount of solvent is 4-30 times and preferably 6-20 times that of the total weight of the raw herbs. The pulverized raw herbs may be immersed in the solvent for 12-48 hours, and preferably 16-36 hours and then be percolated. There is no special limitation to the rate of percolation. Preferably, the rate is 0.5-10 ml/kg raw herbs per minute, and more preferably 1-5ml/kg raw herbs per minute. The effluent liquid is collected and concentrated by vacuum drying or heat drying until the weight of the concentrated solution is 0.5-1.5 (preferably 0.6-1.2) times of the total weight of the raw herbs. The concentrated solution is filtered to remove solid residues. The pH of the filtrate is adjusted to 4-8, preferably 4.5-7.5 by adding a base to obtain the liquid extract of the invention.

In another preferred embodiment, flavoring agents (e.g., sugar), preservative agents (e.g., sodium benzoate) and/or other additives are added into the liquid extract to form an oral solution.

Moreover, the liquid extract can be dried by conventional methods such as spray drying, lyophilization, or concentration-and-drying to obtain solid extract. These solid extracts may be mixed with auxiliary additives or excipients to form various types of drugs, such as tablets, capsules, granules, etc.

In general, the composition of the invention is formed simply by mixing the extract of the invention with suitable carriers. There is no special limitation to the methods for preparing the composition of the invention and various conventional methods in the art, e.g., mixing and the like, are useful in the present invention.

The composition of the invention can be mixed with various carriers to make drug in different forms. The invention covers products in any form that contains the composition of the invention together with pharmaceutically acceptable carriers or excipients.

As used herein, the term "the composition of the invention" includes any pharmaceutical composition or dietary supplement as long as they include the extract of *Semen Trigonellae*, or the extract of *Semen Trigonellae* and other medicinal materials. In one embodiment, the extract of *Semen Trigonellae* or the extract of *Semen Trigonellae* and other medicinal materials comprises 0.1-99 wt %, preferably 1-90 wt %, and most preferably 5-80 wt % of the total weight of the composition. In another embodiment, based on the dry weight of medicinal materials, one gram solid composition or one milliliter of liquid composition is preferably equivalent to 0.1-10 g, more preferably 0.2-5 g, most preferably 0.5-2.5 g of total medicinal materials.

As used herein, the term "pharmaceutically acceptable carrier" refers to a carrier for administering a therapeutic agent and includes various excipients and diluents. The term refers to any pharmaceutical carrier which is not an active ingredient and may be consumed without undue toxicity. Suitable carriers are well known to ordinary people skilled in the pharmaceutical field. A thorough discussion of pharmaceutically acceptable excipients is available in Remington's Pharmaceutical Sciences (Mack Pub. Co., N.J. 1991). Pharmaceutically acceptable carriers may contain liquids such as water, saline, glycerol and ethanol. Additionally, auxiliary substances, such as wetting or emulsifying agents, pH buffering substances, and the like, may also be present.

In addition, the formulation or composition of the invention may also comprise other compounds used in treating or assisting to treat cancers, such as cisplatin. The formulation or composition of the present invention may also be used in conjunction with the chemo-therapeutic or radio-therapeutic means.

The composition of the invention may also comprise at least one pharmaceutically acceptable additive, such as flavoring agent (e.g., sucrose, fructose and the like), preservative agent (e.g., sodium benzoate and the like) and pigment. These additives are well known in the pharmaceutical field.

The extract or composition of the invention can be used to treat various cancers, especially lung cancers. They may be administered in various ways, including, but not limited to, oral, intramuscular, intraperitoneal, intravenous, subcutaneous, or local delivery.

When using composition of the invention, safe and effective amounts of the aqueous or aqueous organic solvent extract of *Semen Trigonellae* (or a mixture comprising *Semen Trigonellae* and other medicinal materials) are administered to mammals. Typically, a safe and effective amount is 0.1-100 grams, preferably 0.5-50 grams of equivalent dry *Semen Trigonellae* per day per person. When mixed medicinal materials are used, the amount is calculated based on the amount of *Semen Trigonellae* in the mixture. Of course, the precise amount will depend upon various factors, such as delivery methods, patient's health, and the like, and is within the scope of skilled clinicians.

The main advantages of the invention are as follow:

(a) The extract of *Semen Trigonellae* has demonstrated its effectiveness in treating lung cancers.

(b) The composition containing the extract of *Semen Trigonellae* and additional medicinal materials has clearly demonstrated its effectiveness in treating lung cancers.

The invention is further illustrated by the following examples. These examples are only intended to illustrate the invention, but not to limit the scope of the invention. For the experimental methods not specified in the following examples, they are performed under routine conditions, or as suggested by the manufacturers.

PREPARATION EXAMPLE NO. 1

The following amount of crude herb material was weighed.

|  | Amount (kg) |
| --- | --- |
| *Semen Trigonellae* | 1 |

The material was cleaned, dried and made into powder with an average grain size of about 250-300 μm. The powder was placed into a cylindrical container having a partition at the bottom (that is, the solvent flowing from top to down and through the powder placed on the partition). The aqueous solution containing 40%(v/v) ethanol was used as solvent. The amount of solvent was 10 times of the total weight of the crude preparation. The crude preparation was mixed with solvent and soaked for 48 hrs before percolation. The rate of percolation was 0.5ml/kg crude preparation per minute. The effluent liquid was collected and concentrated by vacuum drying (<0.05 MPa) so that the weight of the concentrated solution was 5/10 of the total weight of the crude preparation. The concentrated solution was filtered, thereby removing solid residues. The pH of filtrate was adjusted to 5 by adding NaOH solution, thereby obtaining the liquid extract.

Sucrose and sodium benzoate were added into the obtained liquid extract to a final concentration of 5 wt % sucrose and 0.1 wt % sodium benzoate, thereby forming a total amount of 1000 ml for the oral solution A. The concentration was equivalent to 1 gram crude preparation per milliliter.

The solutions containing individual extract of *Astragali Radix, Glehniae Radix, Asparagi Radix, Fructus Ligustri Lucidi,* or *Fructus Corni* were prepared in the similar manner. The concentration of each solution was equivalent to 1 gram crude preparation per milliliter.

PREPARATION EXAMPLE NO. 2 TO NO. 5

The process of Preparation Example No. 1 was repeated except that the following crude preparations were used.

|  | Example No. 2 Amount (kg) | Example No. 3 Amount (kg) | Example No. 4 Amount (kg) | Example No. 5 Amount (kg) | Example No. 6 Amount (kg) |
| --- | --- | --- | --- | --- | --- |
| *Semen Trigonellae* | 1 | 1 | 0.5 | 1 | 3.5 |
| *Astragali Radix* | 2.5 | 20 | 2 | 4 | 3 |
| *Glehniae Radix* | 2.5 | 10 | 2 | 2.5 | 3 |
| *Asparagi Radix* | 1.5 | 1.5 | 5 | 3.5 | 2.5 |
| *Fructus Ligustri Lucidi* | 1 | 0 | 5 | 2 | 1 |
| *Herba Selaginellae Doederleinii* | 2.5 | 0 | 10 | 5 | 1 |

The oral solution B (Example No. 2), oral solution C (Example No. 3), oral solution D (Example No. 4), oral solution E (Example No. 5) and oral solution F (Example No. 6) were prepared, respectively, wherein the concentration of each solution was equivalent to 1 gram of total crude dry preparation per milliliter.

PREPARATION EXAMPLE NO. 6

The procedure of Preparation Example No. 2 was repeated except that a crude preparation was made into powder with an average grain size of 700-850 μm, the aqueous solution containing 60%(v/v) ethanol was used as solvent in an amount of 6 times of the total weight of the crude preparation and the soaking time was 20 hrs. The oral solution G was prepared.

PREPARATION EXAMPLE NO. 7

The procedure of Preparation Example No. 2 was repeated except that the following conditions were used. The rate of percolation was 4ml/kg crude preparation per minute. The effluent liquid was collected and concentrated by vacuum drying (<0.05 MPa) so that the weight of the concentrated solution was 1.4 times of the total weight of the crude preparation. The concentrated solution was filtered, thereby removing solid residues. The pH of the filtrate was adjusted to 7 by adding NaOH solution, thereby obtaining the liquid extract, as oral solution H.

PREPARATION EXAMPLE NO. 8

The procedure of Preparation Example No. 2 was repeated except that the mixture of crude preparation further comprises the following components:

|  | Amount (kg) |
|---|---|
| Herba Salviae Chinensis | 5 |
| Rhizoma Paridis | 1.5 |

Therefore, oral solution I was obtained.

PREPARATION EXAMPLE NO. 9

The procedure of Preparation Example No. 2 was repeated except that the mixture of crude preparation further comprises the following components:

|  | Amount (kg) |
|---|---|
| Herba Salviae Chinensis | 2.5 |
| Rhizoma Paridis | 3 |

Thereafter, oral solution J was obtained.

PREPARATION EXAMPLE NO. 10

The procedure of Preparation Example No. 2 was repeated except that the mixture of crude preparation further comprises the following components:

|  | Amount (kg) |
|---|---|
| Radix Ophiopogonis | 1 |
| Herba Gynostemmae | 1.1 |
| Fructus Corni | 1 |
| Herba Epimedii | 1.2 |

Thereafter, oral solution K was obtained.

PREPARATION EXAMPLE NO. 11

The procedure of Preparation Example No. 2 was repeated except that the mixture of crude preparation comprises the following components:

|  | parts by weight |
|---|---|
| Semen Trigonellae | 0.95 |
| Astragali Radix | 3 |
| Glehniae Radix | 3 |
| Asparagi Radix | 1.5 |
| Fructus Ligustri Lucidi | 1 |
| Herba Selaginellae Doederleinii | 2.8 |
| Herba Salviae Chinensis | 3 |
| Rhizoma Paridis | 1.4 |
| Radix Ophiopogonis | 0.95 |
| Herba Gynostemmae | 0.95 |
| Fructus Corni | 0.95 |
| Herba Epimedii | 0.95 |

Therefore, oral solution L was obtained.

PREPARATION EXAMPLE NO. 12

Preparation of capsules: The procedure of Preparation Example No. 11 was repeated except that the following conditions were used. The extract solution was further vacuum dried (60-70° C), thereby forming solid extract. The solid extract was pulverized, sieved with a 60 mesh screen, mixed with starch powder and packaged into capsules. In this Example, the extract was 60 wt % of the total weight of the composition.

TESTING EXAMPLE NO. 1

The Anti-Tumor Activity of *Semen Trigonellae*

The animal studies were conducted using C57/BL mice, 6-8 weeks of age and a body weight of 18-20 g that were bought from the Animal Center (Jiangsu province, China). Under the sterile conditions, 0.2 ml of solution ($1 \times 10^7$ cell/ml) of cell lines Lewis (lung cancer cell) and S180 (sarcoma) was inoculated into the right armpit of mice. On Day 2 after inoculation, the animals were randomly grouped (10 mice/group). The mice in the experimental group were fed with 0.4 ml extract solution of crude preparation prepared in Example No. 1, solution A (equivalent to 0.4 g dried crude preparation) per day. The mice in the control group were fed with 0.4 ml physiological saline. On Day 14, the mice were sacrificed. The killing activity of NK cell was measured using mice spleen cells as effectors and the tumors were weighed.

The results are shown in the following table, indicating the superior efficiency *Semen Trigonellae* in inhibiting tumor and enhancing immunity.

Moreover, *Astragali Radix, Glehniae Radix, Asparagi Radix, Fructus Ligustri Lucidi, Fructus Corni* also had certain efficiency in inhibiting tumor and/or enhancing immunity.

| Crude preparation | tumor weight (g) | NK activity(%) |
|---|---|---|
| control | 0.63 ± 0.45 | 18.78 ± 2.33 |
| Semen Trigonellae | 0.36 ± 0.24 | 25.61 ± 3.60 |
| Astragali Radix | 0.27 ± 0.20 | 19.43 ± 2.61 |
| Glehniae Radix | 0.58 ± 0.20 | 19.96 ± 5.52 |
| Asparagi Radix | 0.52 ± 0.25 | 25.67 ± 7.88 |
| Fructus Ligustri Lucidi | 0.42 ± 0.25 | 20.78 ± 19.87 |
| Fructus Corni | 0.28 ± 0.03 | 26.30 ± 5.32 |

TESTING EXAMPLE NO. 2

The Anti-Tumor Activity of Composition

Using the same method in Testing Example No. 1, the anti-tumor activity of extracts prepared in Example Nos. 2-11 was tested on the tumor-bearing mice (Lewis cell), except that the test was carried out until Day 21 and the administration dose was 0.5 ml/day, equivalent to 0.5 g total dry medicinal materials (The concentration of each oral solution equals to 1 g total dry medicinal materials/1 ml oral solution).

The results were shown in the following table, indicating the extracts of *Semen Trigonellae* together with other medicinal materials also had superior efficiency in inhibiting tumor.

|   | tumor weight (g) | Transformation rate of lymphocyte (cpm) | NK activity (%) | M ψ cytotoxicity (%) | TH (%) | Ts (%) |
|---|---|---|---|---|---|---|
| saline | 1.76 ± 0.73 | 22755 ± 7744 | 12.97 ± 2.39 | 9.76 ± 0.87 | 49 ± 3 | 28.33 ± 1.52 |
| oral solution B | 1.02 ± 0.74 | 31244 ± 14743 | 20.76 ± 4.10 | 13.16 ± 1.61 | 54.33 ± 1.15 | 25 ± 1 |
| oral solution C | 1.05 ± 0.74 | 30322 ± 13625 | 21.23 ± 3.85 | 14.216 ± 1.52 | 53.25 ± 1.04 | 24.25 ± 1.36 |
| oral solution I | 1.04 ± 1.07 | 36201 ± 21628 | 19.4 ± 2.98 | 13.69 ± 3.47 | 57 ± 1.52 | 25.33 ± 2.08 |
| oral solution L | 0.91 ± 0.41 | 39260 ± 1970 | 20.94 ± 6.87 | 15.55 ± 1.97 | 58 ± 3.16 | 24.74 ± 1.78 |

TESTING EXAMPLE NO. 3

Clinical Test

The clinical test was carried out at Longhua Hospital, an affiliate of the Shanghai University of Traditional Chinese Medicine. 90 volunteer subjects were selected. Each person was checked by chest CT or X-ray, and confirmed to suffer from primary squamous carcinoma of lung or adenocarcinoma of lung or adeno-squamous carcinoma of lung. None of them was treated by surgery or radiotherapy.

The 90 subjects were divided into 3 groups and treated according to the following regime.

| group | regime | Middle survival time (Day) |
|---|---|---|
| botanical composition | Each subject in group of botanical composition treatment was administrated 1-3 dosages of oral solution L (Example No. 11) per day, each dosage equivalent to 2 gram of dry Semen Trigonellae. | 299 days |
| chemotherapy | Each subject in group of chemotherapy treatment was treated according to conventional chemotherapy regime. | 206 days |
| chemotherapy + botanical composition | conventional chemotherapy + 1-3 dosages of oral solution L (Example No. 11) per day, each dosage equivalent to 2 gram of dry Semen Trigonellae. | 312 days |

The clinical results indicated that, the composition of the invention could significantly extend the life span of the lung cancer patients. (p<0.01, compared with chemotherapy treatment group) and improve the quality of life.

All the documents cited herein are incorporated in the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed is:

1. A composition comprising:
    (a) a pharmaceutically acceptable carrier; and
    (b) an effective amount of an aqueous or aqueous organic solvent extract of a crude preparation for treating lung cancer, the crude preparation comprising *Semen Trigonellae*, *Astragali Radix*, *Glehniae Radix*, and *Asparagi Radix*.

2. The composition according to claim 1, wherein the crude preparation further comprises an anti-tumor medicinal material selected from the group consisting of *Fructus Ligustri Lucidi*, *Herba Selaginellae Doederleinii* and combinations thereof.

3. The composition according to claim 2, wherein the crude preparation further comprises an anti-tumor medicinal material selected from the group consisting of *Herba Salviae Chinensis*, *Rhizoma Paridis*, *Salviae Chinensis Herba*, *Herba Hedyotidis Diffusae*, *Radix Sophorae Tonkinensis*, *Radix Sophorae Flavescentis* and combinations thereof.

4. The composition according to claim 3, wherein the crude preparation further comprises an immunity-enhancing medicinal material selected from the group consisting of *Radix Ophiopogonis*, *Herba Gynostemmae*, *Fructus Corni*, *Herba Epimedii*, ginseng, Rhizome of Largehead *Atractylodes*, and combinations thereof.

5. The composition according to claim 4, wherein the crude preparation comprises:
    0.5-5 parts by weight *Semen Trigonellae*, 2-20 parts by weight *Astragali Radix*, 2-10 parts by weight *Glehniae Radix*, 1-5 parts by weight *Asparagi Radix*;
    0.5-5 parts by weight *Fructus Ligustri Lucidi*, 1-10 parts by weight *Herba Selaginellae Doederleinii*;
    1-10 parts by weight *Herba Salviae Chinensis*, 1-5 parts by weight *Rhizoma Paridis*; and
    0.5-10 parts by weight *Radix Ophiopogonis*, 0.5-5 parts by weight *Herba Gynostemmae*, 0.5-5 parts by weight *Fructus Corni*, and 0.5-5 parts by weight *Herba Epimedii*.

6. The composition according to claim 4, wherein the crude preparation comprises:
    0.7-3 parts by weight *Semen Trigonellae*,
    2.5-10 parts by weight *Astragali Radix*, 2.5-6 parts by weight *Glehniae Radix*, 1.2-3.5 parts by weight *Asparagi Radix*;

0.7-3 parts by weight *Fructus Ligustri Lucidi*, 2.5-6 parts by weight *Herba Selaginellae Doederleinii*;

2-8 parts by weight *Herba Salviae Chinensis*, 1.2-3.5 parts by weight *Rhizoma Paridis*;

0.7-5 parts by weight *Radix Ophiopogonis*, 0.7-3 parts by weight *Herba Gynostemmae*, 0.7-3 parts by weight *Fructus Corni*, and 0.7-3 parts by weight *Herba Epimedii*.

7. The composition according to claim 2, wherein the crude preparation comprises 0.5-5 parts by weight *Semen Trigonellae*, 2-20 parts by weight *Astragali Radix*, 2-10 parts by weight *Glehniae Radix*, 1-5 parts by weight *Asparagi Radix*, 0.5-5 parts by weight *Fructus Ligustri Lucidi*, and 1-10 parts by weight *Herba Selaginellae Doederleini*.

8. The composition according to claim 7, wherein the crude preparation further comprises an ingredient selected from the group consisting of 1-10 parts by weight *Herba Salviae Chinensis*, 1-5 parts by weight *Rhizoma Paridis*, 1-5 parts by weight *Salviae Chinensis Herba*, 1-10 parts by weight *Herba Hedyotidis Diffusae*, 1-5 parts by weight *Radix Sophorae Tonkinensis*, 1-5 parts by weight *Radix Sophorae Flavescentis* combinations thereof; and another ingredient selected from the group consisting of 0.5-10 parts by weight *Radix Ophiopogonis*, 0.5-5 parts by weight *Herba Gynostemmae*, 0.5-5 parts by weight *Fructus Corni*, 0.5-5 parts by weight *Herba Epimedii*, 0.5-5 parts by weight ginseng, 0.5-5 parts by weight Rhizome of Largehead *Atractylodes* and combinations thereof.

9. A method for treating lung cancer comprising administering to a subject in need thereof the composition of claim 1.

10. The method according to claim 9, wherein the crude preparation further comprises *Fructus Ligustri Lucidi* and *Herba Selaginellae Doederleinii*.

\* \* \* \* \*